United States Patent [19]

Clyne et al.

[11] Patent Number: 4,841,457
[45] Date of Patent: Jun. 20, 1989

[54] PASTEURIZATION MONITORING PROCESS

[75] Inventors: Carl W. Clyne, St. Louis County; Gary L. Woolever, Madison County; James Teng, St. Louis County; Hooshang Naji, St. Louis, all of Mo.

[73] Assignee: Anheuser-Busch, Incorporated, St. Louis, Mo.

[21] Appl. No.: 71,142

[22] Filed: Jul. 8, 1987

[51] Int. Cl.[4] ................. A61L 2/04; G01K 1/16
[52] U.S. Cl. .................... 364/557; 426/232; 426/407; 426/521; 99/361
[58] Field of Search ........... 364/557; 426/407, 232, 426/521, 11, 13; 422/25; 99/275, 361, 362

[56] References Cited

U.S. PATENT DOCUMENTS

| | | | |
|---|---|---|---|
| 2,282,187 | 5/1942 | Herold et al. | 426/407 |
| 4,263,254 | 4/1981 | Huling | 422/25 |
| 4,279,858 | 7/1981 | Huling | 422/25 |
| 4,331,629 | 5/1982 | Huling | 422/25 |
| 4,441,406 | 4/1984 | Becker et al. | 99/275 |
| 4,684,531 | 8/1987 | Tarterotot | 426/521 X |
| 4,693,902 | 9/1987 | Richmond et al. | 426/407 |
| 4,695,472 | 9/1987 | Dunn et al. | 426/237 |
| 4,727,800 | 3/1988 | Richmond et al. | 99/361 |

Primary Examiner—Parshotam S. Lall
Assistant Examiner—V. N. Trans
Attorney, Agent, or Firm—Gravely, Lieder & Woodruff

[57] ABSTRACT

A process for continuously monitoring a tunnel pasteurizer by observing the spray water temperatures and the time a package is in the tunnel, calculating P.U. input to each package, product cold spot, and average product temperatures in the spray zones, recording and displaying such calculated results, and storing the raw data and calculated results for recall at will in the future.

8 Claims, 6 Drawing Sheets

PASTEURIZATION MONITORING PROCESS

REFERENCE TO PRIOR APPLICATIONS

This application is related to and contains subject matter in common with Ser. No. 620,471, filed June 14, 1984 (now abandoned) and Ser. No. 737,871, filed May 28, 1985, U.S. Pat. No. 4,693,902 which applications are incorporated herein by reference. This is a divisional of co-pending application Ser. no. 926,004 filed on Oct. 31, 1986.

BACKGROUND OF THE INVENTION

Pasteurization has been used in the wine and brewing industry for many years having been developed around 1865 by Louis Pasteur. Pasteurization is the reduction of microorganisms by heating to a limited temperature and holding at that temperature such that there will be minimum effect on physical stability and flavor and a maximum extension of biological stability, thereby increasing shelf life.

Although the present application describes the invention with reference to the pasteurization of beer, the invention also is applicable to all products which are pasteurized in a package, including soda and other soft drinks, fruit juices and drinks, and milk. The specific P.U. inputs and temperatures and times will vary according to the product being treated.

The various organisms in beer are not pathological and dangerous to humans, but affect the taste and appearance of the beer if allowed to grow. Draft beer generally is not pasteurized because it is kept refrigerated and is usually consumed in a short time. However, high quality can and bottle beer traditionally is pasteurized for long shelf life, and conventional type pasteurizers are shown in Herold U.S. Pat. No. 2,282,187 issued May 5, 1942 and Wehmiller U.S. Pat. No. 2,658,608 dated Nov. 10, 1953. Other patents showing pasteurizer and pasteurization processes pertinent to this invention include Becker U.S. Pat. No. 4,441,406, Huling U.S. Pat. No. 4,263,254, Huling U.S. Pat. No. 4,279,858 and Huling U.s. Pat. No. 4,331,629.

In this type pasteurizer, water is sprayed onto the tops of the closely packed packages which are moved through a tunnel which is divided into preheat zones, heating zones, holding zones, and cooling zones. The temperature of the beer in the containers is progressively raised to the desired level before being passed through the cooling zones where it reaches the desired beer out temperature (BOT). The water running off the packages is collected in reservoirs, heated or cooled, and recycled to the sprays or spray pans. These types of tunnel pasteurizers are available in single and double deck configurations.

If pasteurization causes the temperature of the beer to reach too high a level, certain tastes called "pasteurization tastes" can occur in the beer. These are undesirable and have been defined as "bready", "biscuity", "burnt-type tastes", "papery" or "cardboardy". Also, insufficient pasteurization can result in turbidity of the beer or sedimentation.

The organisms which cause the most difficulty in the brewing industry today are actobacillus, pediococcus and wild yeast. These are not pathogenic organisms but can cause turbidity and poor taste in beer. In order to insure complete pasteurization of beer, the temperature of the beer at the so-called "cold spot", which is $\frac{1}{4}''$ from the bottom of the center of the can or bottle, must reach at least 140° F. for a period of time to produce a specified number of pasteurization units (P.U.). It also is desired to pasteurize at the lowest possible peak cold spot temperature (above 140° F.) to avoid overheating the rest of the package contents, because the temperature of the package gets higher as one goes from the cold spot to the top of the package.

The P.U. is a measure of accumulated lethality. One P.U. for beer is one minute at 140° F. Lethality (P.U. per minute) is a rate term which is exponential with temperature. Lethality begins to become significant only when the beer temperature is 130° F. to 135° F. and is most significant at 139° F. and above, although P.U. accumulation begins at 120° F.

Richmond et al. U.S. Pat. No. 4,693,902 describes a process and apparatus for pasteurizing packaged products, specifically beer, with a high spray density and a uniform spray density across the width of the pasteurizer tunnel. The present invention is an improvement on this process in that the variables which go toward determining the P.U. input to the packaged product are monitored and reported to the pasteurizer operator on a predetermined regular basis. The basic processes and apparatus of U.S. Pat. No. 4,693,902 are utilized, but instead of using the conventional P.U. measuring device, continuous readings of the spray water temperature and the speed of the packaged product through the line are recorded and the P.U. is calculated continuously as the product exits the pasteurizer tunnel.

The conventional P.U. measurements device or "P.U. Box" consists of a container having a thermometer wired therein which is connected to a recorder. The wired container is sent through the pasteurizer tunnel and the beer cold spot temperatue is recorded as it progresses through the tunnel. Using the beer cold spot temperature and time, P.U. input is calculated.

This method of measuring P.U. takes approximately 25 minutes to run a can and about 45 minutes to run a bottle through the pasteurizer. The set up time results in a total of only four P.U. Box runs being made through a pasteurizer in an 8 hour shift. The reading also is accurate only for those containers in the same line across the width of the pasteurizer as the P.U. Box container. Thus, only about 500-1000 of approximately 500,000-1,000,000 cans which run through the pasteurizer in an 8 hour shift can be tested and verified for proper pasteurization. Additionally, even though 4 P.U. Box runs per shift per machine are theoretically possible, the manpower required to run this test 4 times per shift around the clock makes it economically unfeasible. Normal testing is only one or two runs per machine per week.

Therefore, instead of less than even 0.1% of the packages being measured for P.U. content (the current practice), this invention provides substantially 100% P.U. measurement and pasteurization verification for the packages leaving the pasteurizer.

Additionally, under the conventional system, pasteurizer conditions are set arbitrarily based on operating experience to obtain the desired pasteurization results. These settings are always conservatively high in an attempt to allow for unexpected problems such as pasteurization down time, unstable temperature control, and although unknown at that time, non-uniform non-optimum spray density, etc., which would adversely affect and change the P.U. input to the product leaving the pasteurizer. These settings are then checked by running a P.U. Box through the pasteurizer at steady state normal operating conditions to verify that normal operation gives the desired pasteurization. This system provides no way to check or verify results under abnormal conditions and, in fact, it is rare if the exact time and circumstances of the abnormal occurrences ae even known.

The P.U. Box system also is subject to operator ability and mechanical failure such as bent probes, the location of the sample in the box, partial "run-out" during the P.U. Box run, down time and low battery charge. A 5 minute down time can add 7.5 P.U.s to the packages.

In the conventional measuring method, it is not unusual for the run of an entire 8 hour shift to be impounded and checked for P.U. input. This requires taste testing or holding the product for a period of up to seven days to determine if anything adverse happened to the packaged product. The checking involves plating, check for turbidity development, etc. With the present system it is easy to identify a specific part of a run that may be adversely affected by the pasteurization conditions and then it is only necessary to isolate that small part of the run for testing. Also, one can recall the data for that portion of the run and recalculate the data if a setting was incorrect for the type of container, etc.

The present process also provides for calculation of the maximum cold spot temperature, which in the case of beer, must reach 140° F. for a minimum of 1 minute to be sure that all portions of the container have been heat treated adequately for pasteurization.

The present process also provides for recording and reporting of the average product out temperature as the product is leaving the pasteurizer. This is important because it is desirable to maintain the product out at approximately the ambient dew point temperature which will avoid condensation forming on the product container which adversely affects the packer process.

Accordingly, it is a principal object of the present invention to provide a process for continuously monitoring a tunnel pasteurization line by continuously monitoring the water spray temperature along the length of the tunnel and monitoring the speed of the packages through the tunnel and using this data to calculate and report the P.U. input, the maximum product cold spot temperature and the average product out temperature of the packages leaving the tunnel at preselected time intervals. It is another object of this invention to record all of this raw data and to be able to retrieve said data at a later time if the operator needs it to determine malfunctions of the pasteurizer.

It also is an important object of this invention to provide a computer system configuration and software approach for implementing the data measurement and storage, data retrieval for calculations, graphical presentations, and automatic report generation for all levels of management.

It also is an object to provide a historical data retention and recall program for repeat presentation and diagnostic procedures as required.

It is also an essential object of this invention to provide the heat transfer data necessary to make the calculations of temperature change versus time in the pasteurizer.

These and other objects and advantages will become apparent hereinafter.

SUMMARY OF THE INVENTION

The present invention comprises a process for continuously monitoring a pasteurizer line and calculating and reporting P.U. input to packages leaving the line at preselected time intervals.

The invention also consists in the parts and in the arrangements and combinations of parts hereinaafter described and claimed.

DESCRIPTION OF THE DRAWINGS

In the accompanying drawings which form part of the specification and wherein like numerals and letters refer to like parts wherever they occur

DETAILED DESCRIPTION

The disclosures of Ser. Nos. 620,471 (abandoned) and 737,871 (now U.S. Pat. No. 4,693,902) show that uniform spray distribution across the width of a pasteurizer and an optimum spray density for bottles and for cans is necessary for pasteurizing product with low P.U. deviation from a desired predetermined figure. Ser. Nos. 620,471 and 737,871 have the objective of achieving a P.U. variation of less than ±2.0 P.U., and a maximum beer cold spot temperature of 140° F. to about 143° F.

The present process is designed to monitor continuously the entire pasteurization process so that if there are any malfunctions in the process or apparatus, the operator will be able to locate and isolate the product affected by such malfunction.

In accomplishing this, the water spray temperature in each of a consecutive series of heating, holding and cooling zones is continuously monitored and recorded. From these data, utilizing heat transfer formulae developed from pilot plant test runs, we calculate and report the P.U. of each product leaving the pasteurizer to the pasteurizer operator. These heat transfer data also are utilized to calculate maximum cold spot temperature in each product as well as the average temperature of the product as it leaves the pasteurizer.

Figure 1:
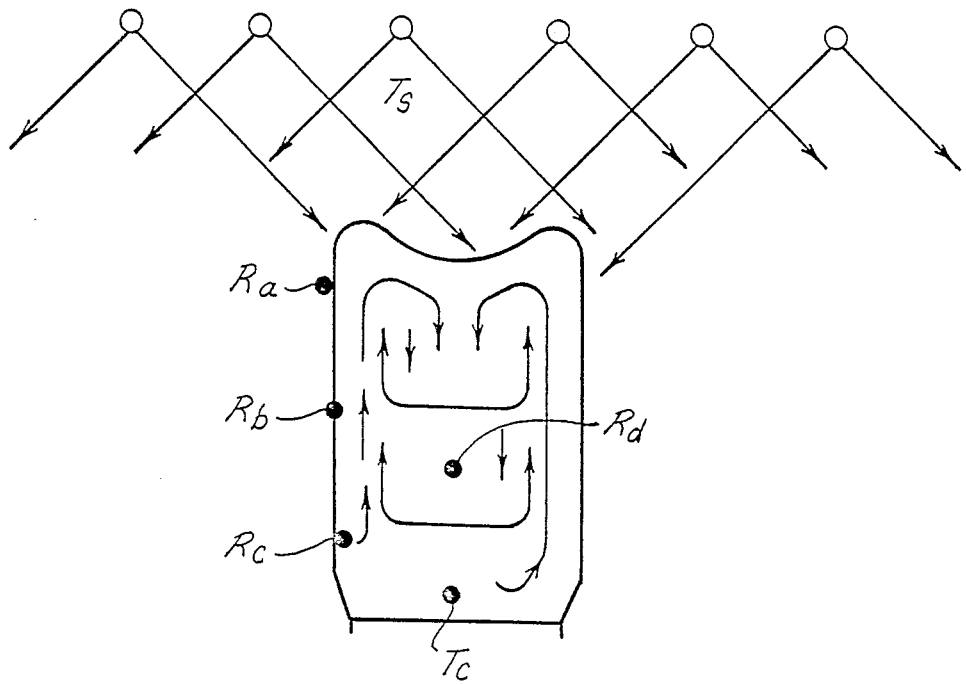
FIG. 1 is a diagrammatic representation of the factors affecting heat transfer to a product in a container being sprayed with water.

FIG. 1 shows a beer can with the different heat transfer resistances shown thereon. The spray water at a temperature $T_s$ is applied to the container and the resistance of the water boundary layer $R_a$ is affected by the spray density. $R_b$ is the resistance of the container. The resistance of the beer boundary layer $R_i$ also is affected by the spray density. $R_d$ is the resistance of natural convection to heat transfer. $T_c$ is the cold spot beer temperature. It is the last point in the can to be heated and is ¼" off the bottom center of the container.

The heat transfer, Q, occurs due to the temperature difference, T, between the hot spray and the cold beer, $T_s - T_c$. The heat is transferred into the container as the spray water runs down the available can area A.

CALCULATION OF HEAT TRANSFER RESULTS

Figure 2:
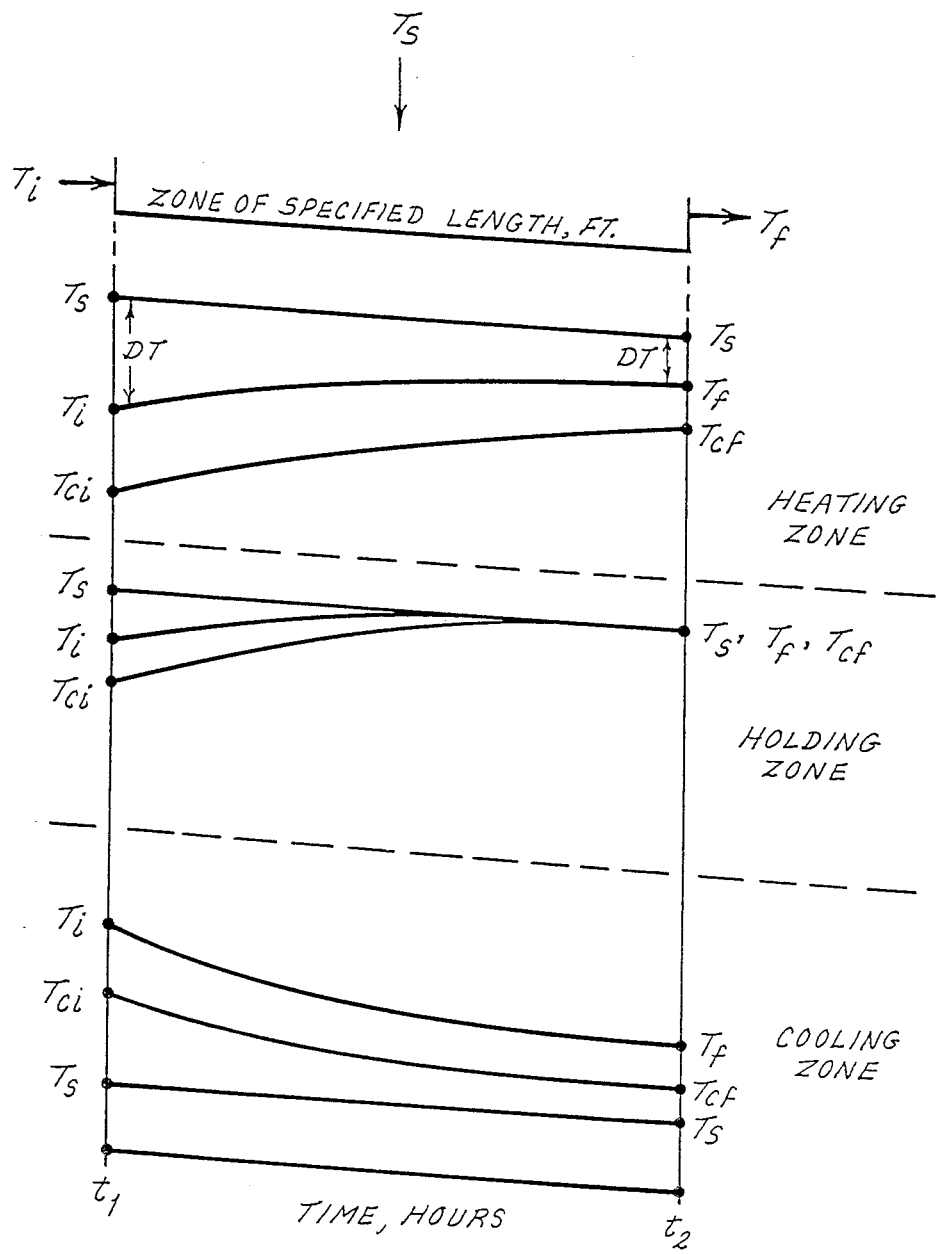
FIG. 2 is a diagrammatic representation of the temperature effect in typical pasteurizer zones as a result of the operations depicted in FIG. 1.

Critical to the calculation of the heat transfer results are the factors illustrated in FIGS. 1 and 2. Following are formulae which define the amount of heat transferred to the product in a container.

$$\text{THE RESISTANCE TO HEAT TRANSFER BY DEFINITION} = R_t + R_a + R_b + R_c + R_d \quad (1)$$

$$\text{THE OVERALL HEAT TRANSFER COEFFICIENT} = U = \frac{1}{R_t} \quad (2)$$

THE HEAT TRANSFERRED IN A ZONE IS $Q$.

$$Q = UA\Delta T \quad (3)$$

Since the spray density directly influences resistance, $R_t$ (Equation 1), it also will affect the overall heat transfer coefficient U (Equation 2). Finally the spray density also influences the amount of heat input into the packages (Equation 3).

Ser. Nos. 620,471 (abandoned) and 737,871 (now U.S. Pat. No. 4,693,902) show that if the spray density is above a predetermined level and is uniform across and along the pasteurizer bed, it produces uniform heating to all packages in the pasteurizer at essentially a maximum value and is not significantly influenced by small fluctuations in the spray density as may be experienced during normal operations.

FIG. 2 shows how temperature changes for spray zones in a typical pasteurizer. Following are definitions of the symbols used in FIG. 2 and hereinafter.

$T_f$ = Product final temp.
$T_i$ = Product initial temp.
t = Time
$t_i$ = Discrete time points for i = 1, 2, 3, ... n
$T_s$ = Spray temp.
$T_c$ = Cold spot temp.
$T_{ci}$ = Cold spot temp. initial
$T_{cf}$ = Cold spot temp. final
$T_t$ = Temp. at time (t)
T = Ave. beer temp.
$T_{c(t)}$ = Cold spot temp. at time t
$T_{(t-ti)}$ = Ave. beer temp. at time (t-$t_i$)
$t_L$ = Time lag in min.
$t_L$ = 3.8 - 0.02 T (t)
$\Delta T = T_s - T$ The heat transfer coefficient "U" is necessary to determine the heat transfer to or from the product in each zone. This is the same for each size and type of product, but differs for cans and bottles and different sizes and shapes of each. The actual temperature changes can be calculated independent of "U" and following is an analysis of the temperature change calculations using the theory of heat transfer by natural convection and laminar flow which are the conditions which most accurately describe the pasteurizer heat transfer process.

Historically, the general formulae, $$Y = CX^m \quad (1)$$

was used by Lorenz to correlate data he obtained in natural convection heat transfer experiments.

Where:

Y = Nusselt number
X = Product of Groshoff and Prandtl numbers
C = Constant
m = 0.25 for laminar fluid flow range The Nusselt, Groshoff and Prandtl numbers are well established dimensionless groups used in the description of transport phenomena.

Substituting the equivalents of Nusselt, Groshoff and Prandtl numbers and the value of m in (1)

$$\frac{h_c L}{K_f} = C \left( \frac{L^3 \rho^2 g \beta \Delta T}{\mu^2} \cdot \frac{C_p \mu}{K_f} \right)^{0.25} \quad (2)$$

Where:

$h_c$ = Coefficient of heat transfer by natural convection
$k_f$ = Thermal conductivity of beer film
L = Geometrical factor
$\rho$ = Density of fluid (beer)
g = Acceleration of gravity
$\beta$ = Coefficient of volumetric expansion (beer)
$\mu$ = Viscosity of fluid (beer)
$C_p$ = Specific heat of fluid (beer)
$\Delta T$ = Difference between surrounding temperature and average product temperature (heat transfer driving force)

At ordinary temperature and pressure range, values of $K_f$, $\rho$, g, $\beta$, $\mu$, and $C_p$ remain nearly constant.

(2) can be simplified to:

$$h_c = C \cdot \Delta T^{0.25} \quad (3)$$

Where:

C = New constant The rate of heat transfer by definition is:

$$Q = h_c \cdot A \cdot \Delta T \quad (4)$$

Where:

Q = Heat transfer rate
A = Area of heat transfer surface

Substituting $h_c$ by its equivalent from (3):

$$Q = C \cdot A \cdot \Delta T^{1.25} \quad (4A)$$

The rate of the heat gain (or loss) by a product is:

$$Q = \frac{T_f - T_i}{t} \cdot W \cdot Sp \quad (5)$$

For a given packaged product, w, Sp and A are constant and equation (6) can be simplified to:

$$T_f - T_i = CT^{1.25} \quad (7)$$

Where:

$T_f$, $T_i$ = The final and initial product temperatures
W = Weight of the product
Sp = Specific heat of the product
t = time Combining (4A) and (5)

$$\left( \frac{T_f - T_i}{t} \right) \cdot W \cdot Sp = C \cdot A \cdot \Delta T^{1.25} \quad (6)$$

where:

C=New constant. The value of C depends on weight size and specific heat of the packaged product. Equation (7) is the general relationship between the rate of product temperature change, $(T_f-T_i)/t$, and differential between the surrounding and average product temperature, $\Delta T$ or driving force.

Substituting $\Delta T$ by $|T_s-T|$ in (7):

$$\left(\frac{T_f - T_i}{t}\right) = C \, |T_s - T|^{1.25} \tag{7A}$$

TIME—TEMPERATURE CORRELATION

The instantaneous rate of a product temperature change from equation (7A) is:

$$\frac{dT}{dt} = C \cdot |T_s - T|^{1.25} \tag{8}$$

Or $$dt = \frac{1}{c} \cdot |T_s - T|^{-1.25} dT \tag{9}$$

Integrating between the initial and final time limits $$\int_i^f dt = \int_i^f \frac{1}{c} \cdot |T_s - T|^{-1.25} dT \tag{10}$$

$$t_f - t_i = \frac{1}{0.25c} (|T_s - T_f|^{-1.25} - |T_s - T_i|^{-0.25})$$

or $$t = \frac{4}{c} (|T_s - T_f|^{-0.25} - |T_s - T_i|^{-0.25}) \tag{11}$$

Where:

$t$ (spray time) $= t_f - t_i$

Rearranging (11) and solving for final temp. $T_f$ $$|T_s - T_f| = \left(\frac{c}{4} \cdot t + |T_s - T_i|^{-0.25}\right)^{-4} \tag{12}$$

In heating process, $T_s > T_i$ $$T_f = T_s - \left[\frac{c_1}{4} \cdot t + (T_s - T_i)^{-0.25}\right]^{-4} \tag{12a}$$

In cooling process, $T_s < T_i$ $$T_f = T_s + \left[\frac{c_2}{4} \cdot t + (T_i - T_s)^{-.025}\right]^{-4} \tag{12b}$$

Values of $c_1$ and $c_2$ are determined from test data developed at research facilities of Anheuser-Busch Companies, Inc. $c_1$ and $c_2$ vary with each type of package and the heating and cooling process.

Cold Spot Correlation

In a cooling process, the cold spot temperature, $T_c$, can be determined from $$T_{cf} = T_s + \left[\frac{c_3}{4} \cdot t + (T_{ci} - T_s)^{-0.25}\right]^{-4} \tag{13}$$

This is the same relationship that was given in equation (12b) for calculating the average beer temperature. The value of "$c_3$" in (13), however, is different from the constant "$c_2$" used in (12b).

In heating process, the cold spot temperature trails the average beer temperature by a time lag, $t_L$.

$$T_c(t) = T(t - t_L) \tag{14}$$

Where:

$T_c(t)$ = cold spot temperature at time t
$T(t-t_L)$ = Averge beer temperature at time $t-t_L$ The value of lag, $t_L$, diminishes at higher temperatures and for the beer temperature range of 40°–160° F. may be estimated from:

$$t_L = 3.8 - 0.02 T(t) \tag{15}$$

Where:

$t_L$ is lag in minutes.

Coefficient "$c_1$", "$c_2$", "$c_3$"

The values of heat transfer coefficients for use in equations (11), (12a), (12b), and (13) have been determined from the test data and computer generated curve fitting calculations.

$c_1$: for average beer temperature calculations, heating
$c_2$: for average beer temperature calculations, cooling
$c_3$: for cold spot temperature calculations, cooling

| Type of Package | $c_1$ | $c_2$ | $c_3$ |
| --- | --- | --- | --- |
| 7 oz NRB* | .13736 | .17038 | .28073 |
| 32 oz NRB | .06409 | .09268 | .16442 |
| 12 oz TRB** | .09105 | .12496 | .13873 |
| 12 oz NRB | .10195 | .13898 | .28384 |
| 16 oz can | .14703 | .23443 | .43943 |
| 12 oz can | .16233 | .24457 | .51327 |

*NRB = Non-returnable bottle
**TRB = Trade return bottle

P.U. Calculations

The pasteurization unit, P.U. is accumulated at the rate of $$P.U./\text{minute} = 10\left(\frac{T_c - 140}{12.5}\right) \tag{16}$$

Where $T_c$ = cold spot temperature, °F.

Total PU:

$$PU = \int_{t_i}^{t_f} 10\left(\frac{T_c - 140}{12.5}\right) dt \tag{17}$$

Where $t_i$ and $t_f$ are the initial and final time limits. $T_c$ as a function of time, f(t), was given in (13) and (14).

The foregoing formulae are programmed into a computer and the data from the pasteurizer is collected and fed into the computer where it is calculated, recorded and reported to the pasteurizer operator.

Based on the foregoing discussion, the following is a typical calculation.

Assume a typical heating zone is diagrammed in FIG. 2.

Given: Current conditions typical for a heating zone $T_s=150°$ F., $T_i=138°$ F., $T_{ci}=134°$ F.

Beer in 12 ounce non-returnable bottles.

$c_1=0.10195$, $C_2=0.13898$, $C_3=0.28384$ Find:
After one minute the final average beer temperature, the final beer cold spot temperature and the number of pasteurization units accumulated during the one minute.

Solution:

Equation (12a)

$$T_f = T_s - \left[\frac{c_1}{4}(t) + |T_s - T_i|^{-0.25}\right]^{-4}$$

Substituting given values.

$$T_f = 150 - \left[\frac{0.10195}{4}(1) + |150 - 138|^{-0.25}\right]^{-4}$$

$T_f = 140°$ F. after one minute

The cold spot temperature will be whatever the average beer temperature was $t_L$ minutes before given by equation (15).

$t_L = 3.8 - 0.02(140)$ $t_L = 1.0$

The temperature $T_i$ one minute before can be calculated by solving equation (119 for $T_i$ and substituting values, but since we already known $T_i$ was 138° F. one minute, ago, we can proceed to the next step.

Equation (16) gives the PU rate/minute.

$$PU/\text{minute} = 10\left(\frac{T_{cf} - 140}{12.5}\right)$$

$T_{cf} = 138°$ F. from last step.

Therefore $$PU/\text{minute} = 10\left(\frac{138 - 140}{12.5}\right)$$

$PU/\text{minute} = 0.692\ PU/\text{minute}$

Since we selected a one minute zone time, the total accumulated P.U. is 1·(0.692) or 0.692 P.U.

From the raw data base we know the spray temperature in each zone for every ten second interval of time for any package moving through the pasteurizer tunnel.

For any exit time we search the raw data base for all spray temperatures and total time that the exiting packages was in the pasteurizer. Then starting at the time the package entered the pasteurizer, we repeat the sequence of calculations for each type of zone in very small time increments. When the calculation is complete, normally 120-150 iterations, the results are displayed on the color operator interface and also stored for later report generation. Much of the intermediate zone data is also stored in separate files for later generation of zone summaries and detailed diagnosis, if required.

Figure 3:
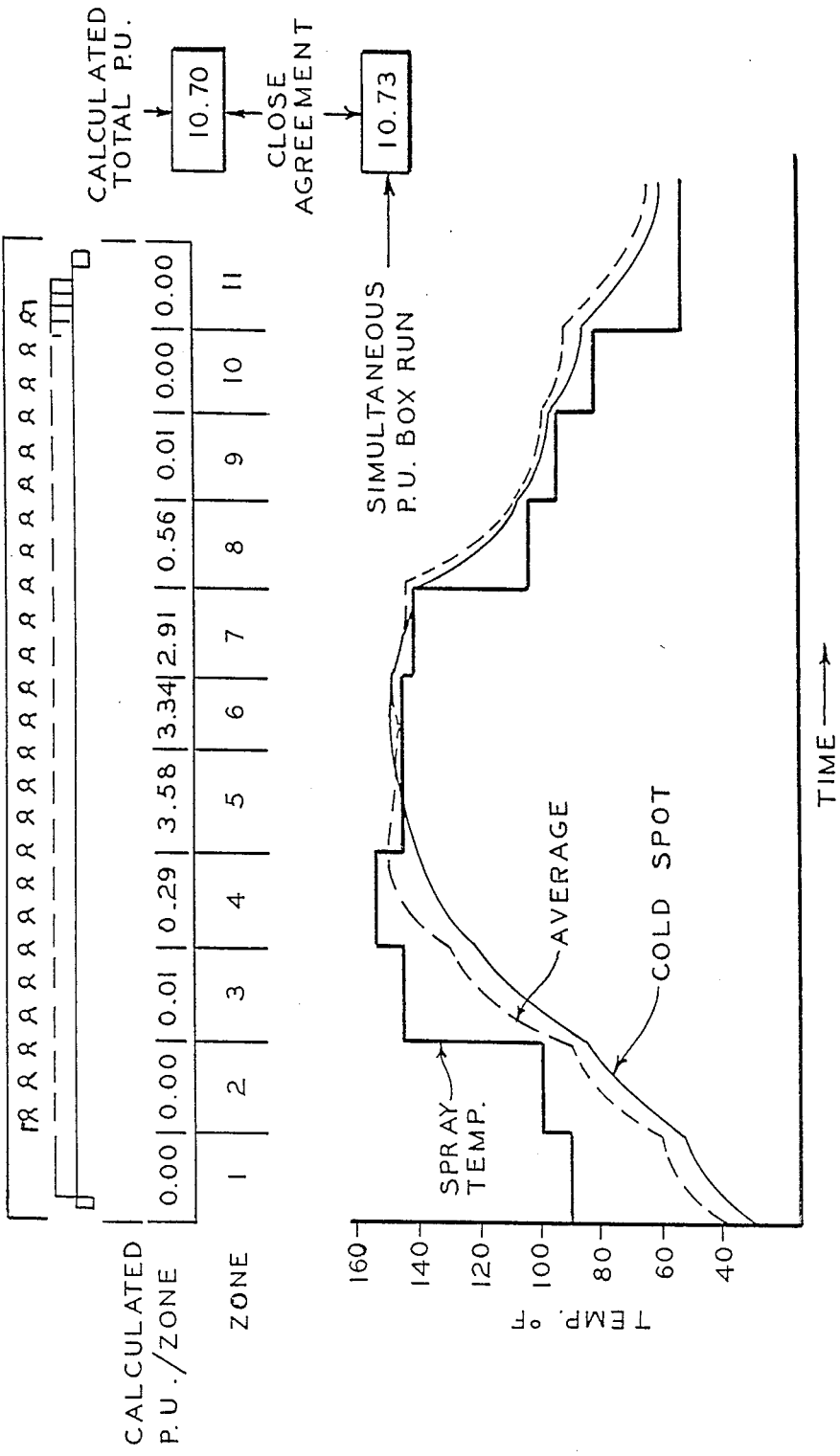
FIG. 3 is a diagrammatic representation of the cumulative temperature versus time effects in a pasteurizer as a product container passes through the pasteurizer.

FIG. 3 shows a chrt of temperature vs. time of a pasteurizer with calculations of P.U. being done using the formula and calculations hereinbefore explained. The run was an equilibrium run with no down time and no skippers. This is compared to P.U. shown in the P.U. Box run according to the prior art. The calculated value is 10.7 P.U. for the specific run shown in FIG. 3 and the observed value is 10.73, which is a close agreement. temperatures were manually recorded and average and cold spot temperatures were calculated. The time was manually recorded in minutes.

Figure 4:
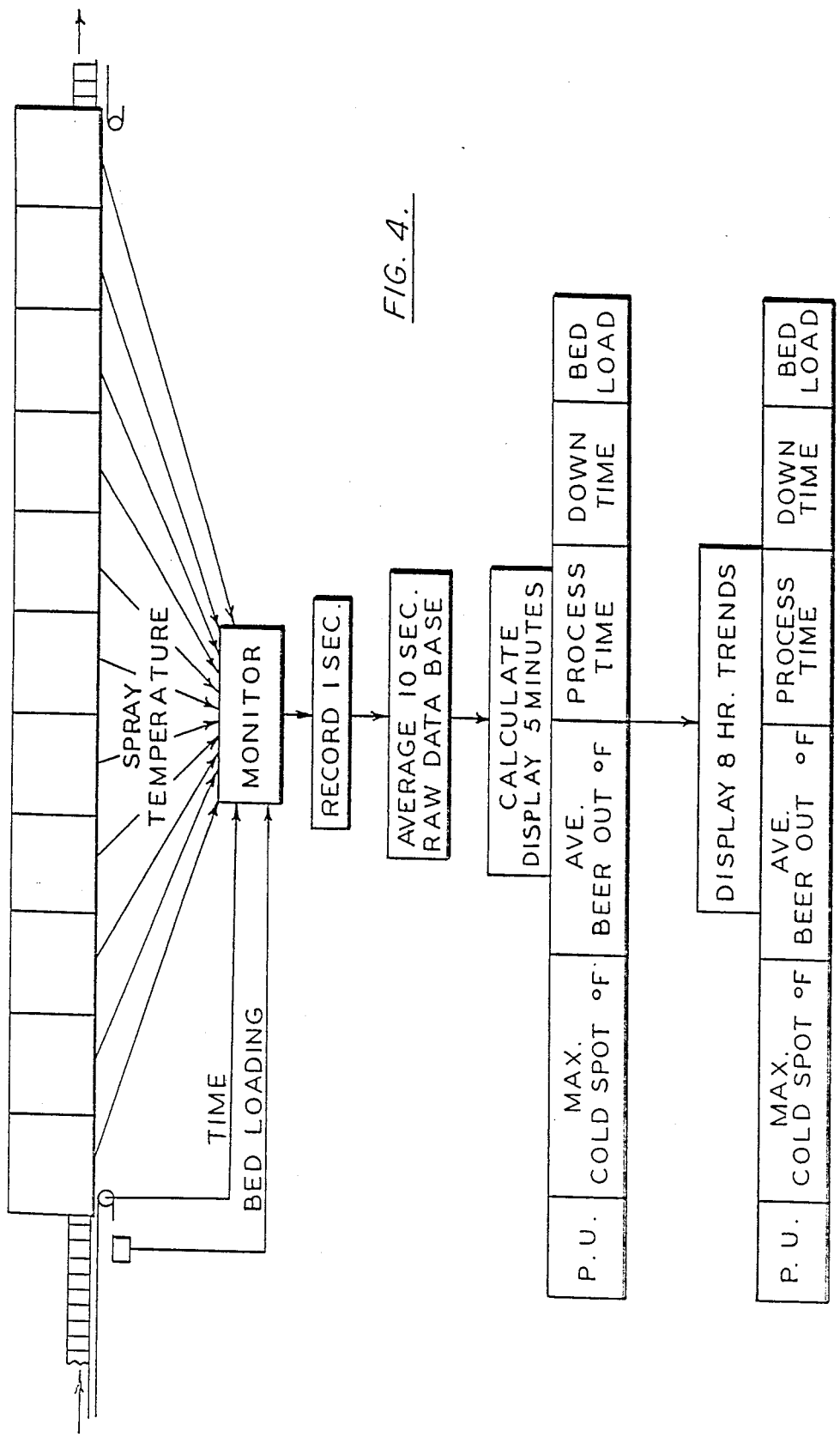
FIG. 4 is an overall flow diagram of the process of this invention.

FIG. 4 shows this process schematically. The spray water temperature $T_s$ from each zone is collected as is the bed laoding as a % of the bed width. Also collected is the walking beam speed which gives the time each product package is in each zone.

These data are recorded at one second intervals and averaged each ten seconds. This data then constitutes a raw data base.

The raw data base is stored in the computer RAM memory and can be called at any time in desired time interval segments.

The raw data is used for computation using the equations hereinbefore set out to calculate the following information which is displayed to the pasteurizer operatior at five minute intervals.

1. Pasteurizer Units (P.U.) to each product package leaving the pasteurizer.
2. Maximum product cold spot temperature.
3. Average beer out temperature.
4. The time each product package spent in the pasteurizer.
5. Down time of the pasteurizer, i.e., the time that the product package did not move in the pasteurizer tunnel.
6. The bed loading as a percentage of bed width.

The computer is programmed to also display at eight hour intervals the trends in each of these variables in both graphical and tabular formats.

Using the data collected from the pasteurizer monitoring system and the calculated data displayed to the operator, one can be certain that each product package leaving the pasteurizer has the required P.U. input and has not received a large or small enough P.U. application to adversely affect the product.

FIG. 4 shows schematically the overall process in which the spray temperature in each zone is monitored as is the time each package is in each zone. Also monitored is the bed loading. In the preferred described process, these data are recorded each second, averaged each ten seconds and the calculated P.U. input, maximum cold spot temperature, average beer out temperature, time in process, bed down time, and bed loading are displayed to the operator each five minutes and displayed at eight hour trends at the end of each eight hour shift.

Figure 5:
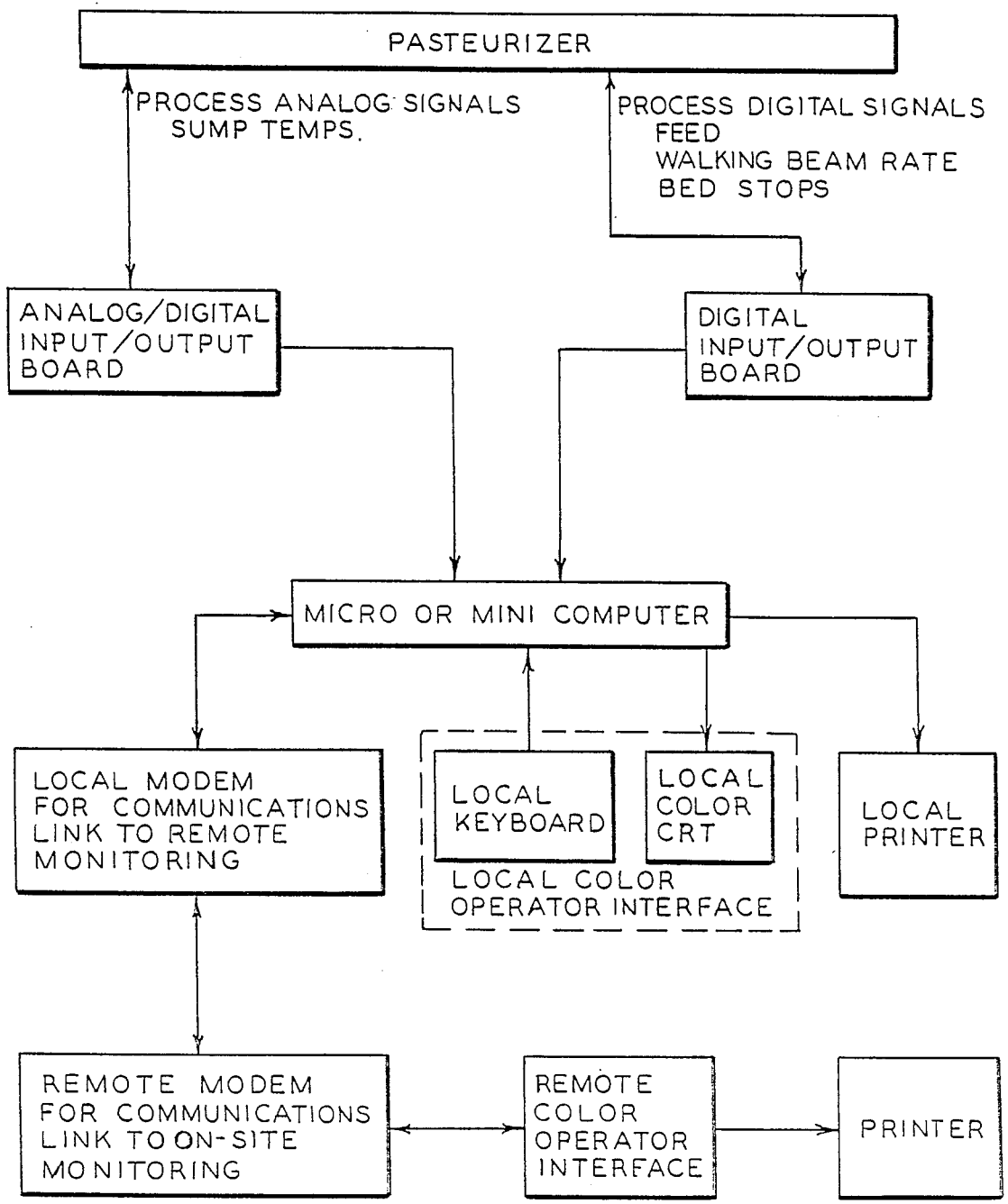
FIG. 5 is a schematic drawing showing the specific system configuration of this invention.

FIG. 5 shows schematically the system configuration in which the spray temperatures are measured by measuring the water temperature of the sumps beneath each zone by analog signals. The product package feed, walking beam rate and bed stops (to measure time in process) are measured by digital signals. These are fed to a mini or microcomputer by way of I/O (input/output) boards. The analog signals are converted to digital signals before being fed into the computer.

The computer is controlled by the local color operator interface (COI) where a keyboard is used to call the specific program up and cause its output to be displayed on the color CRT screen (cathode ray tube) or printed on the local printer.

The computer also is connected to a remote COI and printer by means of modem connection via telephone lines. This allows the on site results to be displayed at a remote location, such as plant office, or even at a location many miles from the plant, as at corporate headquarters.

Figure 6:
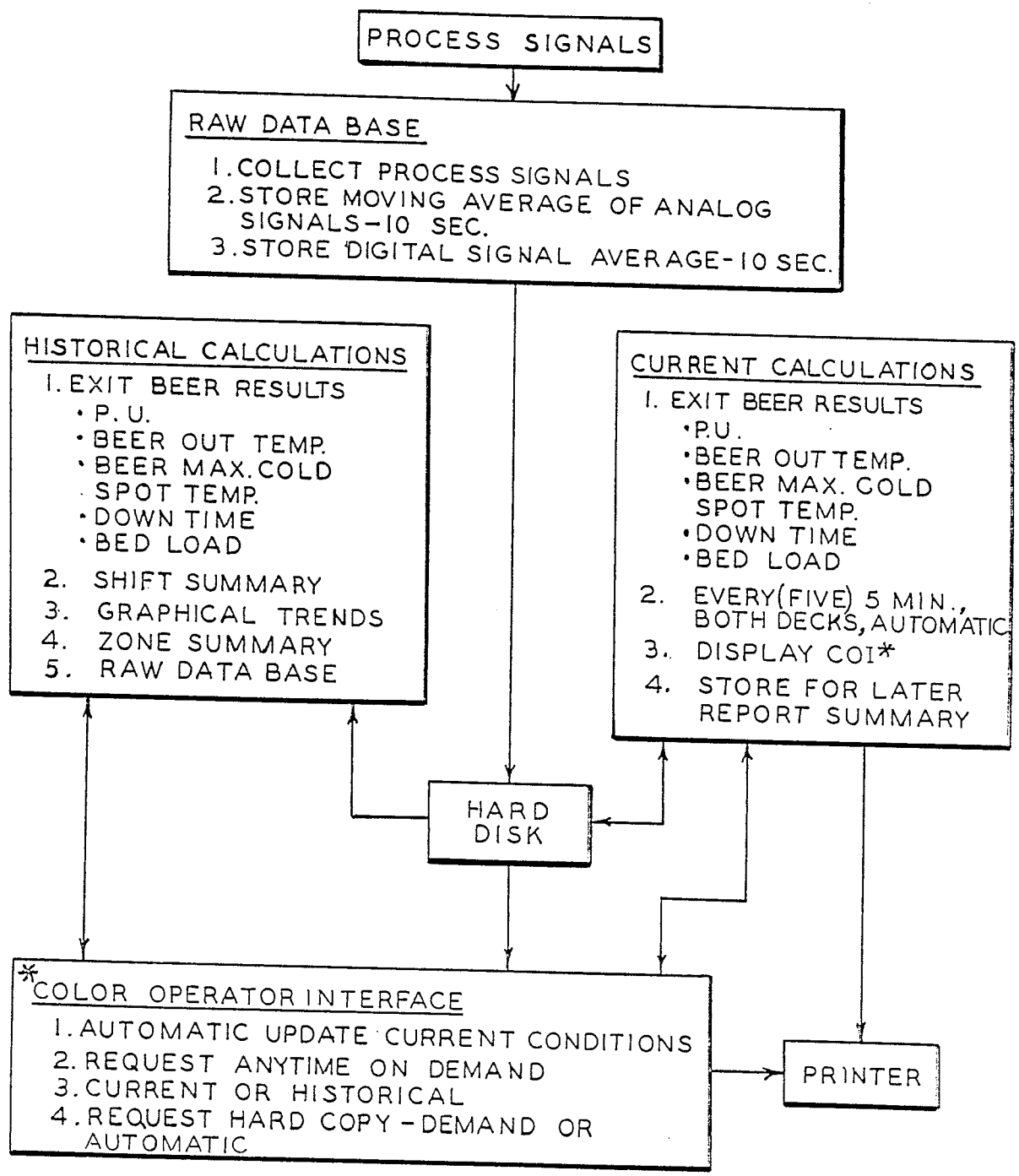
FIG. 6 is a schematic drawing showing the specific program configuration of this invention.

FIG. 6 shows schematically the program configuration. The raw data base, where the ten second averages of the analog and digital signals are collected and stored, is placed on a hard disk. The data base on the hard disk is then used for calculations of both current and historical pasteurization calculations. The current calculations are automatically displayed every five minutes on a printer or on the screen monitored by the operator or both. The current calculations include P.U., beer out temperature, beer maximum cold spot temperature, down time, and bed load. If the pasteurizer is single deck, the results are for the one deck, while if the pasteurizer is double deck, the results for both decks are included. The same information can be requested for any time within the previous 24 hours from the operator console.

The historical calculations include the raw data base and the exit beer results in five minute averages, the eight hour shift summaries, the pasteurizer zone summaries, and the graphical trends. These are all stored on the hard disk as part of the historical calculations and are retrievable on demand by the operator for display or for printing.

This invention is intended to cover all changes and modifications of the example of the invention herein chosen for purposes of the disclosure which do not constitute departures from the spirit and scope of the invention.

What is claimed is:

1. A system for continuously and automatically monitoring a tunnel pasteurizer including
   a tunnel pasteurizer having a finite length divided into a succession of zones and having a finite width and means for passing packages through the tunnel from one end to the other thereof,
   water spray means for spraying water onto packages passing through the tunnel at a uniform spray density across the width of the tunnel and at progressively different temperatures to form a heating zone, a holding zone and a cooling zone from the one end to the other of the tunnel,
   means for continuously measuring spray water temperatures in the zones along the length of the pasteurizer,
   means for continuously measuring the time each package remains in each zone; and
   means responsive to the measured spray water temperatures and measured times each package remains in each zone for empirically determining the P.U. input to each package leaving the pasteurizer tunnel.

2. The system of claim 1 including means for displaying the P.U. input to said packages leaving the pasteurizer tunnel to an operator.

3. The system of claim 1 including means for measuring the product package feed as a percent of the available bed surface.

4. The system of claim 1 wherein the means responsive to the measured spray water temperatures and measured times each package remains in each zone also empirically calculated the maximum cold spot temperature and the average product out temperature in each package leaving the pasteurizer tunnel.

5. The system of claim 4 including means for displaying the maximum cold spot temperature, the average product out temperature and the P.U. input for packages leaving the pasteurizer tunnel to an operator.

6. The system of claim 1 wherein the means responsive to the measured spray water temperatures and measured times each package remains in each zone is connected to a remote location whereby the P.U. input can be monitored at said remote location.

7. The system of claim 1 including means for storing data representing the measured spray water temperatures and measured times each package remains in each zone and means for recalling and displaying said data at will in the future.

8. The system of claim 4 including means for storing data representing the measured spray water temperatures and measured times each package remains in each zone and means for recalling and displaying said data at will in the future.

* * * * *

UNITED STATES PATENT AND TRADEMARK OFFICE
CERTIFICATE OF CORRECTION

Page 1 of 2

PATENT NO.  : 4,841,457

DATED       : June 20, 1989

INVENTOR(S) : Carl W. Clyne, Gary L. Woolever, James Teng, and Hooshang Naji

It is certified that error appears in the above-identified patent and that said Letters Patent is hereby corrected as shown below:

Column 1, line 10, "no." should be "No.".

Column 1, line 42, "U.s." should be "U.S.".

Column 2, line 31, "measurements" should be "measuring".

Column 3, line 6, "ae" should be "are".

Column 4, line 8, "hereinaafter" should be "hereinafter".

Column 4, line 68, "T" should be "$\Delta T$".

Column 5, line 36, "symboles" should be "symbols".

Column 6, line 4, "The Nusselt" should be on the next line.

Column 6, line 35, "The rate of heat transfer by definition is:" should be on the next line.

Column 6, line 55, "$T_f - T_i = CT^{1.25}$" should be "$T_f - T_i = C\Delta T^{1.25}$".

Column 6, line 68, "where:" should be "Where:".

Column 7, line 32,
"$t_f - t_i = \frac{1}{0.25c}\left(\left|T_s - T_f\right|^{-1.25} - \left|T_s - T_i\right|^{-0.25}\right)$" should be
"$t_f - t_i = \frac{1}{0.25c}\left(\left|T_s - T_f\right|^{-0.25} - \left|T_s - T_i\right|^{-0.25}\right)$".

UNITED STATES PATENT AND TRADEMARK OFFICE
CERTIFICATE OF CORRECTION

PATENT NO. : 4,841,457

DATED : June 20, 1989

INVENTOR(S) : Carl W. Clyne, Gary L. Woolever, James Teng, and Hooshang Naji

It is certified that error appears in the above-identified patent and that said Letters Patent is hereby corrected as shown below:

Column 9, line 8, "Find:" should be on the next line.

Column 9, line 36, "(119" should be "(11)".

Column 10, line 1, "chrt" should be "chart".

Column 10, line 9, "The spray" should be inserted before "temperatures".

Column 10, line 9, "the" should be inserted before "average".

Column 10, line 26, "operatior" should be "operator".

Signed and Sealed this

Twenty-fourth Day of July, 1990

Attest:

HARRY F. MANBECK, JR.

*Attesting Officer*     *Commissioner of Patents and Trademarks*